(12) United States Patent
Chattopadhyay et al.

(10) Patent No.: US 6,184,367 B1
(45) Date of Patent: Feb. 6, 2001

(54) **PROCESS FOR THE PRODUCTION OF 4-ARYL-2 BUTANOLS FROM *TAXUS WALLICHIANA***

(75) Inventors: Sunil Kumar Chattopadhyay; Ram Prakash Sharma; Sushil Kumar, all of Lucknow (IN)

(73) Assignee: Council of Scientific and Industrial Research (IN)

( * ) Notice: Under 35 U.S.C. 154(b), the term of this patent shall be extended for 0 days.

(21) Appl. No.: 09/358,113

(22) Filed: Jul. 21, 1999

(30) Foreign Application Priority Data

Mar. 19, 1999 (IN) ............................... 452/DEL/99

(51) Int. Cl.[7] ............................ C07C 39/82; C07H 1/08; C07H 15/18

(52) U.S. Cl. ..................... 536/18.5; 536/4.1; 536/18.6; 568/749; 568/750; 568/751; 568/752; 568/753

(58) Field of Search .................... 536/4.1, 18.5, 536/18.6; 568/749, 750, 751, 752, 753

(56) References Cited

U.S. PATENT DOCUMENTS 4,599,403 * 7/1986 Kumar ................ 536/18.1

* cited by examiner

Primary Examiner—Peter O'Sullivan
(74) Attorney, Agent, or Firm—Perkins Coie LLP

(57) ABSTRACT

The present invention provides a process for the production of two molecules of 4-aryl-2 butanols having the general formula 1 given below:

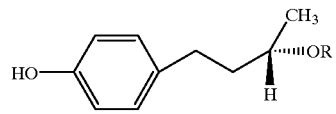

Wherein R=H or glucose from the leaves of *Taxus wallichiana*, which comprises:

(a) defatting air dried, pulverized leaves with aliphatic hydrocarbon solvents, (b) extracting the defatted leaves with chlorinated solvents and polar solvent successively at room temperature, (b) concentrating the chlorinated solvent soluble faction to a residue and treating the residue with aqueous solution of alkali and extracting with chlorinated solvents, (d) acidifying the alkali layer with mineral acid and extracting with ethyl acetate and concentrating the ethyl acetate phase to give compound of formula 1 where R=H, (e) concentrating the polar solvent fraction from step (b) to a residue and treating the residue with aqueous solution of alkali and extracting with chlorinated solvent, and (f) acidifying the alkali phase with mineral acid and extracting with ethyl acetate and concentrating the ethyl acetate to give compound of formula 1 where R=glucose.

7 Claims, No Drawings

PROCESS FOR THE PRODUCTION OF 4-ARYL-2 BUTANOLS FROM *TAXUS WALLICHIANA*

FIELD OF THE INVENTION

This invention relates to a process for production of 4-aryl-2-butanol. The invention particularly, relates to a process for the production of two biologically active molecules (−) betuligenol and (−) betuloside having the general formula (1) as given below:

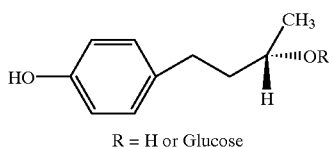

R = H or Glucose

BACKGROUND

Taxol is isolated from the leaves of *Taxus wallichiana*. Taxol, a highly oxygenated diterpenoid molecule and a potent anticancer drug was first isolated from the stem bark of *Taxus brevifolia*. Thereafter, it is also been isolated from other Taxus species including Himalayan yew *Taxus wallichiana*. Various types of cancers have been treated with taxol and the results in the treatment of ovarian and breast cancers are very promising. Taxol has recently been approved by the Food and Drug Administration of the United States for the treatment of ovarian and breast cancers. Taxol, a structurally complicated and chemically labile molecule needing special and careful extraction and separation procedures for its isolation from plant materials. Unfortunately, most of the works are proprietary and have not been published. The American workers have used alcohol to extract taxol from the stem bark of *T. brevifolia* and separation of taxol from the alcoholic extract uses column chromatography over silica with 2% methanol in chloroform as the eluting solvent to yield a mixture of taxol and cephalomannine. Taxol can be separated and isolated from the mixture with a yield of 0.01% either by repeated column chromatography over silica or by high performance liquid chromatography. Taxol has also been isolated from the Himalayan yew *Taxus wallichiana* with a yield of 0.02%. The isolation process involves extracting the stem bark with methanol, partitioning of the methanolic extract between water and chloroform and isolating taxol from the chloroform soluble fraction by chromatography over silicagel.

*Taxus wallichiana* known as the Himalayan yew is available in India. The applicants have investigating the different parts of this plant from different Himalayan regions of India for isolation of naturally occurring analogues of taxol, its important precursors and other biologically active compounds. During the course of investigation the applicants have isolated 2 compounds of 4-aryl-2-butanol namely betuligenol having formula $C_{10}H_{14}O_2$, mp 69–70° C., $[\alpha]_n+$ 20 (C1, MeOH) and betuliloside having formula $C_{16}H_{24}O_7$ mp 187–188°, $[\alpha]_n+22°$ (C1, MeOH) from the leaves of *T. wallichiana*.

Both compounds are known and they have previously been isolated from the plant *Acer nikoense*. No isolation process has been mentioned in the paper (T. Inoue, Y. Ishidate, M. Fujita, M. Kubo, M. Fukushima and M. Nagai, J. Pharm. Soc. Jpn. 98, 41 (1978): Chem, Abstr. 88, 133254 (1978). However, (−) betuligenol, a laevoisomer of the compound of formula 1 where R=H has been isolated by the applicants from the leaves of *Taxus wallichiana*. Now, the applicants have been able to isolate the dextro-isomer of (−) betuligenol which is the compound of formula 1 where R=H. The process of isolation of (−) betuligenol from the leaves of *Taxus wallichiana* involves extraction of leaves with methanol. Isolation of (−) betuligenol with a yield of 0.05% from the methanol extract was achieved by partitioning of the methanol extract between water and chloroform and chromatography of the chloroform soluble fraction over silica gel (S. K. Chattopadhyay V. K. Tripathi. R. S. Thakur, R. P. Sharma and S. P. Jain, *Indian J. Chem* 33B. 409–411 (1994). Compound of formula 1 where R=glucose has not been isolated before from the leaves of *T. wallichiana* although its laevoisomer, betuloside has previously been isolated by the applicants from the leaves of the above plant (S. K. Chattopadhyay et al., *Indian J. Chem.* 33B, 409–411 (1994). The process of isolation of betuloside consists of extraction of the leaves of *T. wallichiana* with methanol, partitioninig of the methanol extract between water and ethyl acetate and column chromatography of the ethyl acetate fraction to give betuloside with a yield of 0.04%. Now, it has recently been reported that both the compounds of formula (1) where R=H or glucose significantly exhibit anti-inflammatory properties by reducing the nitric oxide (NO) production (S. Fushiya, Y. Kabe, Y. Ikegaya and F. Takano, *Planta Medica* 64, 598–602 (1998). Inflammatory macrophages play a key role in inflammatory process by secreting large amount of mediators that control the initiating process of inflammation. Nitric oxide (NO) is one of the critical mediators produced by inducible NO synthase in inflammatory macrophages when stimulated by bacterial products like lipopolysaccharide (LPS) and some cytokines. Nitric oxide (NO) produced by inducible NO synthase plays a role in non specific immune defence against tumors, parasitic fungi, bacteria and protozoa. Moreover, NO is known to be responsible for the hypotension observed in endotoxin shock. Activation of inflammatory macrophages resulting in the production of large amounts of NO is considered to be critical for lethal toxicity. Glucocorticoid and immuno suppressive agents strongly inhibit NO production. Now, it has been reported recently that compounds of formula (1) where R=H or glucose also suppress the NO production. As NO is one of the critical mediators in inflammation, both compounds of formula (1) where R=H or glucose possess significant anti-inflammatory properties by suppressing the production of NO.

During the chemical investigation done by the applicants on the leaves of *T. wallichiana* collected from different parts of India, the applicants have been able to isolate two molecules of 4-aryl-2-butanol compounds of the formula (1) wherein if R=H the compound is (−) betuligenol and wherein if R=glucose the compound is (−) betuloside with yields of 0.2 and 0.2% respectively. Thus, the leaves of *Taxus wallichiana* could be a viable source for the above two important molecules.

OBJECTS OF THE INVENTION

Thus, the main object of the present invention is to provide a process for production of 4-aryl-2-butanols of general formula (1) shown below:

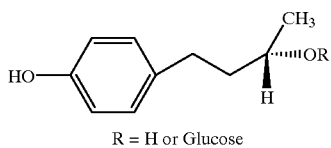

R = H or Glucose which obviates the drawbacks of the earlier methods.

Another object of the present invention is to provide a process which gives the higher yields 0.2% each of these compounds than the known process (0.05 and 0.04% respectively).

Yet another object of the invention is to provide a process which avoids the use of chromatographic separation and makes the process cost effective.

DETAILED DESCRIPTION OF THE INVENTION

Accordingly, the present invention provides a process for production of 4-aryl-2-butanols, of the general formula (1) given below:

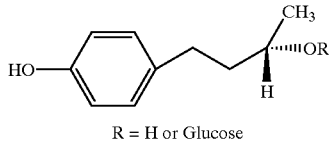

R = H or Glucose from the leaves of *Taxus wallichiana* which comprises: (a) defatting air dried, pulverized leaves with aliphatic hydrocarbon solvents, (b) extracting the defatted leaves with chlorinated solvents and polar solvents successively at room temperature, (c) concentrating the chlorinated solvent soluble fraction to a residue and treating the residue with aqueous solution of alkali and extracting with chlorinated solvent, (d) acidifying the alkali layer with mineral acid and extracting with ethyl acetate and concentrating the ethyl acetate phase to give compound of formula 1 where R=H, (e) concentrating the polar solvent fraction from step (b) to a residue and treating the residue with aqueous solution of alkali and extracting with chlorinated solvent, and (f) acidifying the alkali phase with mineral acid and extracting with ethyl acetate and concentrating the ethyl acetate to give compound of formula 1 where R=glucose.

In one embodiment, the aliphatic hydrocarbon solvent used in step (a) are selected from petroleum ether and hexane.

In another embodiment, the chlorinated solvents used in step (b) are selected from chloroform and dichloromethane.

In another embodiment, the chlorinated solvents used in step (b) are selected from chloroform and dichloromethane.

In yet another embodiment, the polar solvent used in step (b) are selected from methanol, ethanol, acetonitrile, acetone and ethyl acetate.

In a further embodiment, the alkali used in steps (c) and (f) are selected from sodium hydroxide and potassium hydroxide.

In yet another embodiment the mineral acids used in steps (d) and (f) to acidify are selected from hydrochloric acid and sulphuric acid.

The invention is described in detail in the examples given below which are provided to illustrate the invention and therefore should not be construed to limit the scope of the invention.

EXAMPLE 1

Air dried, pulverized, leaves (1 kg) of *Taxus wallichiana* were defatted by percolation at room temperature with petroleum ether (5 lit×3) for three days. The defatted leaves were then extracted with chloroform (5 lit×3) and ethyl acetate (5 lit×3) successively for three days. The chloroform and ethyl acetate extracts were concentrated to give chloroform and ethyl acetate concentrates 30 g and 20 g respectively. The chloroform concentrate (30 g) was dissolved in 1N sodium hydroxide solution (1 lit) with stirring and extracted with dichloromethane (1 lit×3): The aqueous alkali layer was acidified with 1N hydrochloric acid and extracted with ethyl acetate (500 ml×3); The ethyl acetate layer was washed with water, dried over anhydrous sodium sulphate and concentrated to give a residue from which compound of formula 1 (R=H) crystallized out; It was filtered to give pure compound of formula 1 (R=H) (2 g), mp, 69–70° C., $[\alpha]_n+20°$ (C1, MeOH).

The ethyl acetate concentrate (20 g), as obtained above from the defatted plant material by extraction with ethyl acetate, was dissolved in 1N Sodium hydroxide solution (1 lit) with stirring and extracted with dichloromethane (1 lit×3). The aqueous alkali layer was acidified with 1N hydrochloric acid and extracted with ethyl acetate (500 ml×3); The ethyl acetate layer was washed with water, dried over anhydrous sodium sulphate and concentrated to give compound of formula 1 (R=glucose) which recrystallized from acetone-methanol mixture as colourless needles, (2 g), mp. (187–188 C, $[\alpha]n+22°$ (C1, MeOH).

EXAMPLE 2

Air dried, pulverized leaves (1 kg) of *Taxus wallichiana* were defatted by percolation at room temperature with hexane (5 lit×3) for three days. The defatted leaves were extracted with dichloromethane (5 lit×3) and methanol (5 lit×3) successively for three days. The dichloromethane and methanol extracts were concentrated to give dichloromethane and ethanol concentrates 30 g and 20 g respectively. The dichloromethane concentrate (30 g) was dissolved in 1N potassium hydroxide solution (1 lit) with stirring and extracted with chloroform (1 lit×3).

The aqueous alkali layer was acidified with 1N sulphuric acid and extracted with ethyl acetate (500 ml×3). The ethyl acetate layer was washed with water, dried over anhydrous sodium sulphate and concentrated to give a residue from which compound of formula 1 (R=H) crystallized out. It was filtered to give pure compound of formula 1 (R=H) (2 g), mp 69–70° C., $[\alpha]n+22°$ (C1, MeOH).

The methanol concentrate (20 g) as obtained above from the defatted plant material by extraction with methanol, was dissolved in 1N potassium hydroxide solution (1 lit) with stirring and extracted with chloroform (1 lit×3). The aqueous layer was acidified with 1N sulphuric acid and extracted with ethyl acetate (500 ml×3). The ethyl acetate layer was washed with water, dried over anhydrous sodium sulphate and concentrated to give compound of formula 1 (R=glucose) which crystallized from acetone-methanol mixture as colourless needles (2 g), mp (187–188° C., $[\alpha]n+22°$ (C1, MeOH).

Advantages:

1. Defatting the leaves with aliphatic hydrocarbon solvents removes the fatty materials, chlorophyll substances which interferes with the isolation of the above compounds; The compounds could be easily isolated from the defatted materials by eliminating repeated chromatographic separation processes.

2. The selective alkali partitioning during extraction process only extracts the above two molecules leaving behind all other interfering materials. Thus, it makes the process simple and commercially viable.

3. The compounds could be isolated without the use of any chromatographic columns of silicagel or alumina; Thus, the process of production of the two compounds would be simple, cost effective and commercially viable by cutting down the cost of adsorbents, and extra volumes of solvents for its chromatographic separation and purification processes.

What is claimed is:

1. A process for the production of two molecules of 4-aryl-2 butanols having the general formula 1 given below:

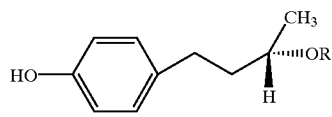

Wherein R=H or glucose from the leaves of *Taxus wallichiana* which comprises:
(a) defatting air dried, pulverized leaves with aliphatic hydrocarbon solvents,
(b) extracting the defatted leaves with chlorinated solvents and polar solvent successively at room temperature,
(c) concentrating the chlorinated solvent soluble fraction to a residue and treating the residue with aqueous solution of alkali and extracting with chlorinated solvents,
(d) acidifying the alkali layer with mineral acid and extracting with ethyl acetate and concentrating the ethyl acetate phase to give compound of formula 1 where R=H,
(e) concentrating the polar solvent fraction from step (b) to a residue and treating the residue with aqueous solution of alkali and extracting with chlorinated solvent, and
(f) acidifying the alkali phase with mineral acid and extracting with ethyl acetate and concentrating the ethyl acetate to give compound of formula 1 where R=glucose.

2. A process as claimed in claim 1 wherein the aliphatic hydrocarbon solvent used in step (a) is selected from petroleum ether (60–80° C.), hexane.

3. A process as claimed in claim 1 wherein chlorinated solvent used in steps (b) and (c) is selected from chloroform and dichloromethane.

4. A process as claimed in claim 1 wherein the polar solvent used in step (b) is selected from methanol, ethanol, acetonitrile, acetone and ethyl acetate.

5. A process as claimed in claim 1 wherein the alkali used in steps (c) and (f) is selected from sodium hydroxide and potassium hydroxide.

6. A process as claimed in claim 1 wherein the mineral acids used in steps (d) and (g) is hydrochloric acid or sulphuric acid.

7. A process as claimed in claim 1 wherein the compounds are (−) betuligenol and (−) betuloside when R=H and R=Glucose respectively.

* * * * *

UNITED STATES PATENT AND TRADEMARK OFFICE
CERTIFICATE OF CORRECTION

PATENT NO. : 6,184,367 B1
DATED : February 6, 2001
INVENTOR(S) : Sunil Kumar Chattopadhyay et al.

Page 1 of 1

It is certified that error appears in the above-identified patent and that said Letters Patent is hereby corrected as shown below:

<u>Title page,</u>
Item [30], Foreign Application Priority Data.

Please delete "March 19, 1999 (IN) 452/DEL/99" and insert -- May 14, 1999 (IN) 734/DEL/99 --.

Signed and Sealed this

Second Day of October, 2001

Attest:

*Nicholas P. Godici*

NICHOLAS P. GODICI
*Acting Director of the United States Patent and Trademark Office*

*Attesting Officer*